United States Patent
Gibson

(10) Patent No.: US 9,700,012 B2
(45) Date of Patent: Jul. 11, 2017

(54) PRO 1272 LETTUCE VARIETY

(71) Applicant: Progeny Advanced Genetics, Inc., Salinas, CA (US)

(72) Inventor: George Darryn Gibson, Prunedale, CA (US)

(73) Assignee: Progeny Advanced Genetics, Salinas, CA (US)

( * ) Notice: Subject to any disclaimer, the term of this patent is extended or adjusted under 35 U.S.C. 154(b) by 0 days.

(21) Appl. No.: 14/826,080

(22) Filed: Aug. 13, 2015

(65) Prior Publication Data

US 2016/0044886 A1   Feb. 18, 2016

Related U.S. Application Data

(60) Provisional application No. 62/036,981, filed on Aug. 13, 2014.

(51) Int. Cl.
*A01H 5/12* (2006.01)

(52) U.S. Cl.
CPC ........................ *A01H 5/12* (2013.01)

(58) Field of Classification Search
None
See application file for complete search history.

(56) References Cited

U.S. PATENT DOCUMENTS 8,692,073 B2 * 4/2014 Gibson .................. A01H 5/12
435/410

OTHER PUBLICATIONS

Enza Zaden Web site product catalogue, May 13, 2005, and Osborne Seed Company catalogue web site.*

* cited by examiner

*Primary Examiner* — Eileen O Hara
(74) *Attorney, Agent, or Firm* — Kilpatrick Townsend & Stockton LLP

(57) ABSTRACT

A new lettuce variety designated 'PRO 1272' is described. 'PRO 1272' is a green leaf lettuce variety exhibiting stability and uniformity.

11 Claims, No Drawings

PRO 1272 LETTUCE VARIETY

CROSS REFERENCE TO RELATED APPLICATION

This application claims the benefit under 35 §USC 119(e) of prior U.S. Provisional Patent Application No. 62/036,981, filed Aug. 13, 2014, the disclosure of which is hereby incorporated by reference in its entirety.

FIELD

This invention relates to the field of plant breeding. In particular, this invention relates to new lettuce, *Lactuca sativa*, variety, 'PRO 1272'.

BACKGROUND

Lettuce is an increasingly popular crop. Worldwide lettuce consumption continues to increase. As a result of this demand, there is a continued need for new lettuce varieties. In particular, there is a need for improved green leaf lettuce varieties that exhibit improved growth habits, bolting and tip burn tolerance, and disease resistance.

SUMMARY

In order to meet these needs, the present invention is directed to an improved green leaf lettuce variety with a medium green color and open growth habit that produces a high number of uniform leafs, and improved tolerance to bolting and tip burn as well as resistance to Tomato bushy stunt virus (tombusvirus). In particular, the present invention is directed to lettuce, *Lactuca sativa*, seed designated as 'PRO 1272' having ATCC Accession Number PTA-122481. The present invention is further directed to a *Lactuca sativa* plant produced by growing 'PRO 1272' lettuce seed having ATCC Accession Number PTA-122481. The present invention is further directed to a lettuce head isolated from a *Lactuca sativa* plant produced by growing 'PRO 1272' lettuce seed having ATCC Accession Number PTA-122481. The present invention is further directed to a *Lactuca sativa* plant having all the physiological and morphological characteristics of a *Lactuca sativa* plant produced by growing 'PRO 1272' lettuce seed having ATCC Accession Number PTA-122481. The present invention is further directed to an F1 hybrid *Lactuca sativa* plant having 'PRO 1272' as a parent, where 'PRO 1272' lettuce seed is grown from 'PRO 1272' seed having ATCC Accession Number PTA-122481.

The present invention is further directed to lettuce, *Lactuca sativa* plants and lettuce heads isolated therefrom produced by growing 'PRO 1272' lettuce seed. The present invention is further directed to a *Lactuca sativa* plant and the lettuce head isolated therefrom having all the physiological and morphological characteristics of a *Lactuca sativa* plant produced by growing 'PRO 1272' lettuce seed having ATCC Accession Number PTA-122481. The present invention is further directed to an F 1 hybrid lettuce, *Lactuca sativa* plant and a head isolated therefrom grown from the seed having 'PRO 1272' as a parent wherein 'PRO 1272' is grown from 'PRO 1272' lettuce seed having ATCC Accession Number PTA-122481.

The present invention is further directed to pollen isolated from 'PRO 1272' lettuce plants. The present invention is further directed to ovules isolated from 'PRO 1272' lettuce plants. The present invention is further directed to tissue culture of 'PRO 1272' lettuce plants.

The present invention is further directed to a method of selecting lettuce comprising a) growing PRO 1272 lettuce plants wherein the plants are grown from lettuce seed having ATCC Accession Number PTA-122481 and b) selecting a plant from step a). The present invention is further directed to lettuce plants and seeds produced there from wherein the lettuce plant is isolated by the selection method of the invention. The present invention is further directed to a method of selecting lettuce plants by: a) growing more than one 'PRO 1272' lettuce plant, where the plants are grown from lettuce seed having ATCC Accession Number PTA-122481; and b) selecting a plant from step a). The present invention is further directed to lettuce plants and seeds produced therefrom, where the lettuce plants and seeds are isolated by the selection method of the invention.

The present invention is further directed to a method of breeding lettuce by crossing a lettuce plant with a plant grown from 'PRO 1272' lettuce seed having ATCC Accession Number PTA-122481. The present invention is further directed to lettuce plants, heads isolated therefrom, and seeds produced therefrom, where the lettuce plant is isolated by the breeding method of the invention

DETAILED DESCRIPTION

Definitions

In order to more clearly understand the invention, the following definitions are provided:

Green Leaf Lettuce: Green leaf lettuce is *Lactuca sativa* L. The plant develops in an upright open growing habit with medium textured leaves. The leaves are typically somewhat savoyed, and while the shape can vary by variety. Leaf margins are often undulated or frilled. Other leaves range in color from light green to dark green with a minimal midrib Inner heart leaves are typically smaller and lighter green in color.

Core Length: Core length is the length of the internal lettuce stem. Core length is measured from the base of the cut head to the tip of the core.

Core Diameter: Core diameter is the diameter of the lettuce stem at the base of the cut head.

Green Leaf Heart: Green leaf heart is the densest part of the green leaf plant often yellow and light green in color and of succulent texture. The heart is generally enclosed by two to three outer darker green leaves.

Heart Length: Heart length is the length of the vertically sliced lettuce plant as measured from the base of the cut stem to the top leaf margin of the longest outermost leaf that encloses the green leaf heart.

Head Length:Core Length Ratio: The ratio of the head length to core length is indicative of the percentage of useable product produced by the lettuce plant.

Plant Diameter: The plant diameter is a measurement across the top of the lettuce plant at its widest point. The measurement of frame diameter is taken from the outer most leaf tip horizontally to the outer most leaf tip.

Head Weight: Head weight is the weight of the marketable lettuce plant, cut and trimmed to market specifications.

Rogueing: Rogueing is the process in lettuce seed production where undesired plants are removed from a variety. The plants are removed because they differ physically from the general desired expressed characteristics of the variety. The differences can be related to size, color, maturity, leaf texture, leaf margins, growth habit, or any other characteristic that distinguishes the plant.

Market Stage: Market stage is the stage when a lettuce plant is ready for commercial lettuce harvest. In the case of a Green Leaf lettuce variety, a Green Leaf plant is at a marketable state when the heart has some density and the head has reached an adequate size and weight.

Tomato Bushy Stunt: Lettuce dieback was first observed in California in the mid-1980s, and reports of the disease have increased over the last 10 years. Complete crop losses have occurred in fields of green leaf lettuce, and no commercial green leaf cultivar has been shown to be resistant to the disease. In the U.S., green leaf is a rapidly growing market segment, having increased 68% over the last five years (USDA, 2002). The disease has occurred in commercial fields of some leaf lettuce cultivars; however, symptoms have never been observed on any modern crisphead (iceberg) cultivars. Lettuce dieback is caused by several related tombusviruses including Tomato bushy stunt virus (TBSV) and lettuce necrotic stunt virus (LNSV) (Liu et al., 1999; Obermeier et al., 2001). These are soil borne, highly stable, and mechanically transmitted, and have no known vector. The conditions affecting symptom development remain poorly understood. The disease is frequently observed in low-lying areas of fields with a prior history of flooding, suggesting that the virus may be carried in river water and/or that disease symptoms may be associated with increased root stresses such as those presented by excess moisture. No effective cultural or chemical control methods have yet been identified.

Resistance to Tomato Busy Stunt refers to a level of resistance in a lettuce variety as measured by visual symptoms. Resistance is deemed present when symptoms are not present in at least 95% of a lettuce variety when exposed to Tomato Bushy Stunt virus.

Taking into account these definitions, the present invention is directed to seeds of the lettuce variety 'PRO 1272', plants produced by growing 'PRO 1272' lettuce seeds, head isolated or harvested from the plants, one or more plants selected from a collection of 'PRO 1272' plants and seeds derived or produced therefrom; plants produced by crossing a lettuce plant with a 'PRO 1272' lettuce plant and seeds derived or produced therefrom.

Origin and Breeding History of the Variety 'PRO 1272'

'PRO 1272' is an open growing green leaf variety that produces a high number of leaves that are uniform in size and shape. This variety is distinct and unique to all other green leaf lettuce varieties due to its combined disease and physiological resistances. 'PRO 1272' has a unique and valuable resistance, as it is resistant to Tomato bushy stunt virus (TBSV), a very problematic disease found throughout the Salinas and Imperial valleys of California. In addition to this disease resistance, 'PRO 1272' is also resistant to the physiological problems associated with lettuce production in areas of higher temperatures such as internal tip burn and fringe burn, and an improved resistance to bolting.

'PRO 1272' is a green leaf lettuce variety developed from a hand pollinated cross of two proprietary breeding lines. The two parental varieties were selected for their specific disease and physiological resistances, and their respective adaptations, and their leaf shape. The cross was made in Year 1, and through the single seed descent breeding method, we have developed a slightly savoyed and slow to medium growing green leaf variety with a high leaf count, good weight, a desired rectangular leaf shape, and a low core. 'PRO 1272' is resistant to Tomato bushy stunt virus (TBSV). Through extensive field trialing and screenings, 'PRO 1272' has demonstrated resistance to TBSV and resistance to tip burn and fringe burn, while being slower bolting than other TBSV-resistant green leaf varieties.

In a Year 1 research greenhouse, a cross was made of two proprietary green leaf breeding lines. The parent lines were selected for their resistances, their shape and structure and their adaptability. The F1 seed was harvested in the fall of Year 1 and designated as C003X2002.

In Year 2, 20 F1 seeds of C003X2002 were planted in a research green house facility in Watsonville Calif., indicated by research line number PWAT107973. The F1 plants were allowed to self-pollinate, the F2 seed was then harvested in bulk. The seed was immediately cleaned, processed, blended, and prepared for planting.

One hundred random F2 seeds of line number PWAT107973 were again planted in the research green house facility in Watsonville Calif. and redesignated as PWAT108056. Segregation amongst the F2 population was noted and all plants were allowed to self-pollinate and produce seed. The F3 seed from each plant was harvested and packaged individually in the fall of Year 2. One seed from each package (plant) was removed and placed in one envelope and designated as PWAT118972, and planted again in the research greenhouse facility. The F3 plants were evaluated at multiple stages of maturity, where segregation for phenotype and maturity was again evident and noted, and all plants were allowed to self-pollinate and produce seed. F4 seed from 100 individual plants was harvested, cleaned, and packaged individually.

The 100 F4 lines, all from nonselected single F3 plants of the pedigree C003X2002, were processed in a California facility. A trial was prepared containing each of the 100 F4 individual lines of the designated pedigree, the parent varieties, and susceptible and resistant standard varieties as checks for the multiple diseases. A research trial was planted twice in the Salinas valley, California in spring of Year 4 in fields known to be infected with Tomato bushy stunt virus. The trials were evaluated in summer of Year 4. All F4 lines were evaluated based on phenotypic uniformity, improved leaf size and shape, improved weight, bolting resistance, and improved tolerances to tip burn and fringe burn when compared to the parent and check varieties. The F4 lines were also rated on their resistance to TBSV. After multiple evaluations of the trials, 3 F4 lines of this pedigree were selected as they outperformed the parent varieties, their sibs, and the majority of other lines in the trial for the designated traits. PWAT118972-4 B/S was among the 3 F4 lines advanced, and was increased in a summer research and development seed production crop. The F5 seed was harvested in bulk in the fall of Year 5, designated as PSJV129511. The production block was rogued at multiple stages of maturity and designated as uniform and stable.

The 3 F5 lines of this pedigree, including line number PSJV129511, along with their parent lines and check varieties were evaluated in multiple trials in the lettuce production regions of California and Arizona. Multiple fields in the California trials were known to harbor the Tomato bushy stunt virus. The F5 lines were screened for resistance to the diseases present, as well as tip burn and fringe burn. Yield traits such as weight, core length, leaf count, leaf size, and leaf shape were also evaluated. PSJV129511 continued to be resistant to TBSV, while having a low core and being free of the symptoms associated with tip and fringe burn. This line also rated higher than its sister lines for leaf size, leaf shape and leaf count.

Based on the trial data, and the disease resistance, seed from PSJV129511 was again increased in a San Joaquin valley, California research and development seed production crop in a block containing roughly 1000 plants. The block was rogued at multiple stages of maturity, and was noted as uniform and stable. Large trials of the F6 were conducted in the major production regions of California and Arizona. The variety continued to demonstrate the desired disease and physiological resistances, as well as express improved leaf size, shape and count.

A larger seed increase was made, and the F7 seed was harvested. The production crop was rogued at multiple stages of maturity and was noted to be uniform, stable and free of variants.

As evaluated in 1 multiple seed production fields and commercial plantings, 'PRO 1272' has been observed for two generations to be uniform and stable without variants.

As described herein, lettuce variety 'PRO 1272' has numerous distinguishing characteristics.

Breeding and Selection

The present invention is further directed to the use of 'PRO 1272' lettuce in breeding and selection of new varieties.

A. Breeding

In lettuce breeding, lines are selected for certain desired appropriate characteristics. For example, one line may be selected for bolt tolerance in the fall growing conditions of the desert production locations of California and Arizona, or for resistance to viruses such as Tomato bushy stunt virus (TBSV). Another line may be selected for the size, color, and texture of the lettuce head. Crosses are made, for example, to produce a medium to light green, tip burn resistant green leaf lettuce with improved texture, and size for spring and summer harvest in the Salinas valley of California.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

In addition to manual removal of anther tubes, a modified method of misting to wash the pollen off prior to fertilization may be used to assure crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908.

B. Selection

In addition to crossing, selection may be used to identify and isolate new lettuce lines. In lettuce selection, lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

DEPOSIT INFORMATION

A deposit of the lettuce variety 'PRO 1272' is maintained by Progeny Advanced Genetics, having an address at 590A Works Street, Salinas, Calif. 93901, United States of America. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety made according to the Budapest Treaty in the American Type Culture Collection, (ATCC), ATCC Patent Depository, 10801 University Boulevard, Manassas, Va., 20110, USA.

The lettuce variety PRO 1272' was deposited on Aug. 20, 2015 according to the Budapest Treaty in the American Type Culture Collection (ATCC) Patent Depository, 10801 University Boulevard, Manassas, Va., 20110, USA. The deposit has been assigned ATCC number PTA-122481. Access to this deposit will be available during the pendency of this application to persons determined by the Commissioner of Patents and Trademarks to be entitled thereto under 37 C.P.R. §1.14 and 35 U.S.C. §122. Upon allowance of any claims in this application, all restrictions on the availability to the public of the variety will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

This invention will be better understood by reference to the following non-limiting Examples.

EXAMPLES

Example 1: General Trialing Method

The following steps illustrate the general trialing method of the invention:

I. Set Up
1. A trial is set up to compare one or more lines. Parental lines and related varieties are identified.
2. Primary slots are identified.
3. Necessary accession lines are located and purchased/received from seed dealers or growers.
4. All varieties are assigned a number to maintain integrity and anonymity.
5. Trials are set up in with all necessary varieties. Variety arrangement for trial is diagramed.

II. Planting
1. Commercial plantings are located by contacting commercial growers during the planting slot recommended for the variety.
2. A field is located during commercial planting and the necessary rows and area is marked off.
3. Varieties are planted according to a diagram, generally in 100 foot ranges.
4. All varieties are planted in same manner to mimic the planting of the commercial variety as closely as possible.
5. A trial map is drawn diagramming the trial, the trial location in the field and directions to the field.

III. Maintenance
1. All varieties are treated identically. Plants are watered, fertilized, and treated to control pests in the same manner as other lettuce plants in the commercial field.

2. The trial is thinned to separate the plants for optimum growth.

IV. Evaluation

1. Evaluations are done as near to the time of the commercial harvest as possible.
2. The evaluation is conducted "blindly". The evaluator(s) do not have the key to the trial at the time of evaluation.
3. 24 heads of each variety are evaluated.
    a. The frame diameter of 24 random plants are measured to the nearest cm.
    b. 24 mature plants of each variety are cut to the cap leaf.
    c. The following measurements are then conducted and recorded:
        1. Each plant is weighed to the nearest gram.
        2. The core diameter of each head is measured to the nearest mm.
        3. The heads are then sliced in to halves, discarding 1 half
        4. The core lengths (from the cut stem to the core tip) are measured to the nearest mm.
        5. The plant length (from the cut stem to the cap leaf) is measured to the nearest mm.
        6. The plant diameter (at its widest point) is measured to the nearest mm.
        7. The heart length is measured to the nearest mm.
        8. The ideal maturity or harvest date is then estimated based on the solidity of the plant, the core length and any other physiological characteristics present.
        9. The leaf color is documented using the Munsell Color Charts for Plant Tissue.
    d. From these measurements, an Excel program is used to calculate the averages, the standard deviations and the T-Tests for the compared varieties.

varieties. Comparative data was obtained and analyzed for the different green leaf lettuce lines. Days to maturity, leaf count and head weight were compared.

'PRO 1272' is a new and distinct variety of green leaf lettuce that most closely resembles the variety 'Big Star'. 'PRO 1272' has a medium green color and a high number of leaves that are uniform in size and shape. This variety has a medium growth rate, and forms a medium sized plant with excellent pliability.

The most distinguishing characteristics of 'PRO 1272' are unique multiple resistances and improved adaptability to multiple end uses. 'PRO 1272' is resistant to the Tombusvirus known as Tomato bushy stunt virus (TBSV). 'PRO 1272' is further distinguished from other similar TBSV-resistant varieties due to its improved resistance to bolting, and high number of leaves that are uniform in size and shape.

'PRO 1272' most closely resembles the green leaf variety 'Big Star', but is most notably distinct by its resistance to TBSV. 'PRO 1272' is also 3 to 4 days faster maturing than 'Big Star', produces a heavier plant weight, and has a higher leaf count.

Evaluation of Days to Maturity

TABLE 1

| Trial Evaluation Monte Location | 1 May Soledad, California | | 2 July Chualar, California | | 3 August Gonzales, California | |
|---|---|---|---|---|---|---|
| Plant | 'PRO 1272' | 'Big Star' | 'PRO 1272' | 'Big Star' | 'PRO 1272' | 'Big Star' |
| Days to Maturity | 71 | 74 | 53 | 55 | 60 | 63 |

Example 2: Comparative Analysis

Following the procedures of Example 1, 'PRO 1272' green leaf lettuce was compared to its parent and standard As shown in the results listed in Table 1, the days to maturity of 'PRO 1272' is approximately three days faster than that of 'Big Star'.

Evaluation of Leaf Count

TABLE 2

| Trial | 1 | | 2 | | 3 | |
|---|---|---|---|---|---|---|
| Wet/Eval Date Location | March 8   May 19 Soledad, California Leaf count | | May 22   July 14 Chualar, California Leaf count | | June 26   August 26 Gonzales, California Leaf count | |
| Plant | 'PRO 1272' | 'Big Star' | 'PRO 1272' | 'Big Star' | 'PRO 1272' | 'Big Star' |
| 1 | 32 | 28 | 30 | 27 | 30 | 29 |
| 2 | 32 | 28 | 30 | 27 | 30 | 29 |
| 3 | 30 | 30 | 32 | 27 | 30 | 28 |
| 4 | 32 | 27 | 31 | 26 | 31 | 28 |
| 5 | 32 | 26 | 31 | 28 | 30 | 28 |
| 6 | 33 | 28 | | | 31 | 27 |
| 7 | 32 | 28 | | | 31 | 28 |
| 8 | 32 | 28 | 31 | 27 | 30 | 27 |
| 9 | 31 | 27 | 31 | 29 | 30 | 27 |
| 10 | 33 | 28 | 31 | 29 | 31 | 25 |
| 11 | 31 | 26 | 30 | 27 | 29 | 26 |
| 12 | 33 | 26 | 29 | 28 | 31 | 28 |
| 13 | 33 | 27 | 29 | 27 | 30 | 27 |

TABLE 2-continued

| Trial | 1 | | 2 | | 3 | |
|---|---|---|---|---|---|---|
| Wet/Eval Date | March 8 | May 19 | May 22 | July 14 | June 26 | August 26 |
| Location | Soledad, California | | Chualar, California | | Gonzales, California | |
| | Leaf count | | Leaf count | | Leaf count | |
| Plant | 'PRO 1272' | 'Big Star' | 'PRO 1272' | 'Big Star' | 'PRO 1272' | 'Big Star' |
| 14 | 33 | 28 | 30 | 29 | 30 | 26 |
| 15 | 32 | 28 | 29 | 29 | 31 | 26 |
| 16 | 32 | 27 | 30 | 25 | 31 | 25 |
| 17 | 32 | 27 | 30 | 28 | 32 | 29 |
| 18 | 31 | 26 | 29 | 28 | 32 | 28 |
| 19 | 30 | 26 | 29 | 27 | 32 | 26 |
| 20 | 33 | 28 | 30 | 27 | 31 | 26 |
| Average | 32.0 | 27.4 | 30.1 | 27.5 | 30.7 | 27.2 |
| Stan dev | 9.45E−01 | 1.04E+00 | 9.00E−01 | 1.10E+00 | 8.13E−01 | 1.27E+00 |
| T test | 3.30E−17 | | 4.44E−09 | | 1.16E−12 | |
| Probability % | 100.00 | | 100.00 | | 100.00 | |
| % Difference | −16.8 | | −9.5 | | −12.9 | |
| Confidence Int | 0.046 | 0.051 | 0.046 | 0.051 | 0.046 | 0.051 |

As shown in the results listed in Table 2, the average leaf count of 'PRO 1272' is significantly greater than that of 'Big Star'.

Evaluation of Head Weight

TABLE 3

| Trial No. | 1 | | 2 | | 3 | |
|---|---|---|---|---|---|---|
| Wet/Eval Date | March 8 | May 19 | May 22 | July 14 | June 26 | August 26 |
| Location | Soledad, California | | Chualar, California | | Gonzales, California | |
| | Head weight (g) | | Head weight (g) | | Head weight (g) | |
| Plant | 'PRO 1272' | 'Big Star' | 'PRO 1272' | 'Big Star' | 'PRO 1272' | 'Big Star' |
| 1 | 486 | 400 | 489 | 400 | 503 | 425 |
| 2 | 501 | 389 | 501 | 425 | 498 | 405 |
| 3 | 489 | 412 | 502 | 435 | 432 | 487 |
| 4 | 512 | 400 | 523 | 456 | 496 | 468 |
| 5 | 468 | 428 | 489 | 489 | 478 | 425 |
| 6 | 479 | 395 | | | 482 | 464 |
| 7 | 425 | 389 | | | 469 | 424 |
| 8 | 498 | 425 | 498 | 425 | 472 | 404 |
| 9 | 510 | 416 | 478 | 400 | 491 | 415 |
| 10 | 501 | 451 | 469 | 412 | 489 | 462 |
| 11 | 499 | 425 | 512 | 397 | 460 | 482 |
| 12 | 516 | 400 | 501 | 367 | 452 | 400 |
| 13 | 444 | 378 | 497 | 386 | 506 | 425 |
| 14 | 448 | 386 | 486 | 429 | 514 | 412 |
| 15 | 500 | 394 | 487 | 404 | 482 | 406 |
| 16 | 471 | 365 | 446 | 423 | 501 | 451 |
| 17 | 436 | 412 | 458 | 412 | 502 | 401 |
| 18 | 425 | 387 | 479 | 423 | 514 | 423 |
| 19 | 468 | 396 | 489 | 400 | 498 | 387 |
| 20 | 448 | 369 | 498 | 395 | 465 | 368 |
| Total infected | 476.2 | 400.9 | 489.0 | 415.4 | 485.2 | 426.7 |
| Stan dev | 2.97E+01 | 2.12E+01 | 1.85E+01 | 2.74E+01 | 2.17E+01 | 3.23E+01 |
| T test | 2.87E−11 | | 4.98E−11 | | 5.77E−08 | |
| Probability % | 100.00 | | 100.00 | | 100.00 | |
| % Difference | −18.8 | | −17.7 | | −13.7 | |
| Confidence Int | 0.046 | 0.051 | 0.046 | 0.051 | 0.046 | 0.051 |

As shown in the results listed in Table 3, the average head weight in grams (g) of 'PRO 1272' is significantly greater than that of 'Big Star'.

Evaluation of TBSV Resistance

Resistance to Tomato bushy stunt virus (TBSV) was determined by growing the test variety (PRO 1272') against known susceptible varieties (e.g., 'Big Star') in fields where TBSV is present. The test plots were made as equivalent as possible using standard field plotting techniques and resistance is defined by visible infection. Infected plants can be severely stunted and mature, diseased plants may only reach 6 to 8 inches in height. The outermost leaves are extensively yellowed. The younger, inner leaves often remain dark green in color, but can be rough and leathery in texture. In some cases, the older leaves develop necrotic spotting that can turn into extensive areas of brown, dead tissue. There is no partial infection to provide relative scoring. The plants are either infected and scored with a '1' and die, or not infected and scored with a '0'. The results are shown in Tables 4A and 4B.

TABLE 4A

| Trial No. | 1 | | 2 | |
|---|---|---|---|---|
| Wet Date | March 8 | | May 22 | |
| Location | Soledad, California | | Chualar, California | |
| Plant | Mortality from TBSV | | Mortality from TBSV | |
| | 'PRO 1272' | 'Big Star' | 'PRO 1272' | 'Big Star' |
| 1 | 0 | 0 | 0 | 0 |
| 2 | 0 | 1 | 0 | 0 |
| 3 | 0 | 1 | 0 | 1 |
| 4 | 0 | 1 | 0 | 1 |
| 5 | 0 | 0 | 0 | 1 |
| 6 | 0 | 0 | 0 | 1 |
| 7 | 0 | 0 | 0 | 1 |
| 8 | 0 | 0 | 0 | 1 |
| 9 | 0 | 1 | 0 | 1 |
| 10 | 0 | 1 | 0 | 1 |
| 11 | 0 | 1 | 0 | 1 |
| 12 | 0 | 0 | 0 | 1 |
| 13 | 0 | 1 | 0 | 0 |
| 14 | 0 | 0 | 0 | 0 |
| 15 | 0 | 1 | 0 | 0 |
| 16 | 0 | 0 | 0 | 0 |
| 17 | 0 | 1 | 0 | 0 |
| 18 | 0 | 0 | 0 | 1 |
| 19 | 0 | 1 | 0 | 0 |
| 20 | 0 | 1 | 0 | 1 |
| 21 | 0 | 1 | 0 | 0 |
| 22 | 0 | 1 | 0 | 1 |
| 23 | 0 | 0 | 0 | 1 |
| 24 | 0 | 0 | 0 | 1 |
| 25 | 0 | 0 | 0 | 1 |
| 26 | 0 | 1 | 0 | 0 |
| 27 | 0 | 1 | 0 | 1 |
| 28 | 0 | 1 | 0 | 1 |
| 29 | 0 | 1 | 0 | 1 |
| 30 | 0 | 1 | 0 | 1 |
| Average | 0 | 0.6 | 0 | 0.666666667 |
| Stan dev | 0 | 0.498272879 | 0 | 0.479463301 |
| T test | 1.39655E−08 | | 2.7042E−10 | |
| Probability | 100.00 | | 100.00 | |
| % Mortality | 0.0 | 60.0 | 0.0 | 66.7 |

TABLE 4B

| Trial No. | 3 | |
|---|---|---|
| Wet Date | June 26 | |
| Location | Gonzales, California | |
| Plant | Mortality from TBSV | |
| | 'PRO 1272' | 'Big Star' |
| 1 | 0 | 0 |
| 2 | 0 | 1 |
| 3 | 0 | 1 |
| 4 | 0 | 1 |
| 5 | 0 | 0 |
| 6 | 0 | 1 |
| 7 | 0 | 1 |
| 8 | 0 | 1 |
| 9 | 0 | 0 |
| 10 | 0 | 0 |
| 11 | 0 | 0 |
| 12 | 0 | 0 |
| 13 | 0 | 1 |
| 14 | 0 | 0 |
| 15 | 0 | 1 |
| 16 | 0 | 1 |
| 17 | 0 | 1 |
| 18 | 0 | 0 |
| 19 | 0 | 1 |
| 20 | 0 | 0 |
| 21 | 0 | 0 |
| 22 | 0 | 1 |
| 23 | 0 | 0 |
| 24 | 0 | 1 |
| 25 | 0 | 1 |
| 26 | 0 | 0 |

TABLE 4B-continued

| | Trial No. 3 Wet Date June 26 Location Gonzales, California Plant Mortality from TBSV | |
|---|---|---|
| | 'PRO 1272' | 'Big Star' |
| 27 | 0 | 1 |
| 28 | 0 | 0 |
| 29 | 0 | 0 |
| 30 | 0 | 1 |
| Average | 0 | 0.533333333 |
| Stan dev | 0 | 0.507416263 |
| T test | 3.4166E−07 | |
| Probability | 100.00 | |
| % Mortality | 0.0 | 53.3 |

As shown in the results listed in Tables 4A and 4B, 'PRO 1272' is significantly more resistant to TBSV as compared to 'Big Star'.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed:

1. *Lactuca sativa* seed designated as 'PRO 1272', representative sample of seed having been deposited under ATCC Accession Number PTA-122481.

2. A *Lactuca sativa* plant produced by growing the seed of claim 1.

3. A lettuce head isolated from the plant of claim 2.

4. A *Lactuca sativa* plant having all the physiological and morphological characteristics of the *Lactuca sativa* plant of claim 2.

5. An $F_1$ hybrid *Lactuca sativa* plant having 'PRO 1272' as a parent where 'PRO 1272' is grown from the seed of claim 1.

6. Pollen of the plant of claim 2.

7. An ovule of the plant of claim 2.

8. Tissue culture of the plant of claim 2.

9. A method of selecting lettuce, comprising:
   a) growing more than one plant from the seed of claim 1; and
   b) selecting a plant from step a).

10. A *Lactuca sativa* plant selected by the method of claim 9.

11. *Lactuca sativa* seed produced from the *Lactuca sativa* plant of claim 10.

* * * * *